US00PP35716P3

(12) United States Plant Patent
Meilland

(10) Patent No.: US PP35,716 P3
(45) Date of Patent: Apr. 2, 2024

(54) CLIMBING ROSE PLANT NAMED 'MEIBRITTY'

(50) Latin Name: *Rosa hybrida*
Varietal Denomination: MEIBRITTY

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 62 days.

(21) Appl. No.: 18/134,605

(22) Filed: Apr. 14, 2023

(65) Prior Publication Data

US 2024/0008377 P1 Jan. 4, 2024

(30) Foreign Application Priority Data

May 30, 2022 (QZ) ..... PBR 2022/1337

(51) Int. Cl.
*A01H 5/02* (2018.01)
*A01H 6/74* (2018.01)

(52) U.S. Cl.
USPC ..... Plt./114
CPC ..... *A01H 6/749* (2018.05)

(58) Field of Classification Search
USPC ..... Plt./114
CPC ..... A01H 6/749; A01H 5/02
See application file for complete search history.

(56) References Cited

U.S. PATENT DOCUMENTS

PP6,892 P 7/1989 Meilland
PP7,215 P 4/1990 Austin

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of rose plant, referred to by its cultivar name, 'MEIBRITTY', is disclosed. The new variety forms attractive, very double cream-ochre colored center and pink colored towards the external petals colored flowers. Attractive glossy foliage is formed, which contrasts beautifully with the blossoms. A climbing growth habit is displayed. The new variety is well suited for providing attractive ornamentation in the landscape.

1 Drawing Sheet

Latin name of genus and species of plant claimed: *Rosa hybrida.*

Variety denomination: 'MEIBRITTY'.

CROSS REFERENCE TO RELATED APPLCIATIONS

This application claims priority to Plant Breeders' Right Application Number 2022/1337, which was filed at Community Plant Variety Office in the European Union on May 30, 2022, the contents of which are hereby incorporated by reference for all purposes.

STATEMENT REGARDING PRIOR DISCLOSURES BY THE INVENTOR

The first offer for sale of the new variety was Jul. 28, 2022, in France. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of climbing rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'KORHOKHEL' variety (not patented). The male parent (i.e., the pollen parent) of the new variety was the 'AUSCOT' variety (U.S. Plant Pat. No. 07,215).

The parentage of the new variety can be summarized as follows:

'KORHOKHEL' X 'AUSCOT'

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, hardwood cuttings, and semi-hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms flowers with a cream-ochre colored center and pink colored towards the external petals,
(b) produces very double flowers, and
(c) exhibits a climbing growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORHOKHEL' variety (i.e., the seed parent) produces less petals compared to the new variety. In addition, the 'AUSCOT' variety (i.e., the pollen parent) displays a shrub growth habit, whereas the new variety displays a climbing growth habit. Moreover, the new variety can be readily distinguished from other similar non-parental varieties. For example, the 'MEIVIOLIN' variety (U.S. Plant Pat. No. 06,892) produces flowers that are medium pink in color, whereas the new variety produces flowers that are cream-ochre colored in the center and pink colored towards the external petals.

The new variety has been named 'MEIBRITTY'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately two years of age and were observed during September while budded on Rosa Laxa and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of two-years-old specimens of the new variety during September while budded on Rosa Laxa and growing outdoors at Le Cannet des Maures, Var, France.

Botanical classification: *Rosa hybrida* cultivar MEIBRITTY.

Commercial classification: Climbing Rose Plant.

Plant:

*Habit.*—Climbing.

*Height.*—Typically between 150 cm to 200 cm.

*Width.*—Typically between 150 cm to 200 cm.

Branches:

*Color.*—Young stems: commonly near a color between Yellow-Green Group 144A and 144B, more or less covered with near Greyed-Purple Group 184B. — adult wood: commonly near a color between Yellow-Green Group 144A and 144B; anthocyanin coloration is absent.

*Length.*—From the crown to the flower is typically between 100 cm to 110 cm.

*Diameter*—Approximately 0.5 cm on average.

*Thorns.*—Configuration on adult stems: upright and very elongated to slight concave on the upper surface; and concave on the under surface. — long prickles — quantity: commonly between 20 to 25 thorns per 10 cm long young stem and commonly between 20 to 25 thorns per 10 cm long adult stem. — long prickles — length: typically between 0.5 cm to 0.8 cm on young stems and approximately 0.5 cm on adult stems. — long prickles — base shape: elliptical. — long prickles — color on young stems: commonly near a color between Yellow-Green Group 144C and Yellow-Green Group 146D, more or less suffused with near Greyed-Purple Group 184C going toward the base. — long prickles — color on adult stems: commonly near Greyed-Orange Group 166A suffused with near Greyed-Orange Group 166B toward the apex. — small prickles — quantity: absent.

*Internode.*—Numbers on the entire branch: typically between 30 to 40. — length: typically between 2.0 cm and 3.0 cm.

Foliage:

*General appearance.*—Very dense, with a glossy aspect.

*Number of leaflets.*—3, 5, 7; most often 7.

7 *leaflets leaf.*—Length: typically between 10 cm to 12 cm. — width: approximately 7.0 cm on average.

*Terminal leaflet.*—Length: typically between 4.0 cm to 5.0 cm. — width: approximately 3.0 cm on average.

*New foliage.*—Upper surface color commonly near a color between Green Group 141A with Yellow-Green Group 146A. — under surface color commonly near Green Group 143B broadly covered with near Greyed-Purple Group 184B.

*Adult foliage.*—Upper surface color commonly near a color between Green Group 137A and Green Group 139A. — under surface color commonly near Green Group 137C. — anthocyanin coloration: absent.

Leaflets:

*Shape.*—Top: acuminate. — base: obtuse.

*Glossiness of upper surface.*—Medium.

*Texture.*—Upper surface is smooth, under surface is bumpy.

*General appearance.*—Oval.

*Serration.*—Small and single.

*Undulation on the margin.*—Weak.

*Venation.*—Color is commonly near Yellow-Green Group 144B and pattern is imparipinnate.

*Petiole rachis.*—Color of upper surface: commonly near Green Group 143A. — color of under surface: commonly near Yellow-Green Group 144A. — texture: upper surface is glandular, under surface is slightly glandular with little prickles. — rachis of terminal leaflet: length is typically between 4.5 cm to 6.0 cm and diameter is approximately 0.1 cm on average.

*Petioles.*—Upper surface: few glandular. — under surface: few prickles. — color of upper surface: commonly near Yellow-Green Group 144B. — color of under surface: commonly near Yellow-Green Group 144A more or less shaded with near Greyed-Purple Group 184B. — length: approximately 2.0 cm on average. — diameter approximately 0.1 cm on average.

*Stipules.*—Length: approximately 1.2 cm on average. — width: approximately 0.5 cm on average. — general appearance: rather broad but very curling. — texture: smooth. — color of upper surface: commonly near Green Group 141A on the edges, evolving to Yellow-Green Group 144B toward the petiole. — color of under surface: commonly near Green Group 143A.

Inflorescence:

*Number of flowers per stem.*—Between 3 and 5 flowers per stem.

*Lastingness of the bloom.*—On the plant: approximately 10 days on average. — in vase: not tested.

*Bud.*—Shape: globular. — size: medium. — length: approximately 2.0 cm on average. — width: approximately 2.5 cm on average. — color as calyx breaks: upper surface: on the external petals commonly near Red-Purple Group 65A slightly suffused with near Red-Purple Group 68A on the edges; on the internal petals commonly near a color between Red-Purple Group 65B and Red Group 49A. basal spot upper surface: very little and near Yellow Group 3C on the external petals and near Yellow Group 5C on the internal petals. under surface: on the external petals commonly near Red-Purple Group 65A strongly covered with near Red-Purple Group 68A; on the internal petals commonly near Red-Purple Group 65A strongly covered with a color between Red-Purple Group 68A and Red Group 51B. basal spot under surface: very little and near Yellow Group 5C on the external petals and near Yellow Group 5B on the internal petals.

*Sepals.*—Number commonly 5. — length: approximately 1.5 cm on average. — width: approximately 0.7 cm on average on the median part. — shape: at the top: few elongated and rather broad. at the base: flat at union with the receptacle. — extensions: commonly 2 sepals without extensions and 3 sepals with very weak extensions. — upper surface: texture: tomentous. color commonly near Green Group 143A covered with many hairs that are commonly near Green-White Group 157C. — under surface: texture: smooth (slightly glandular on edges). color commonly near Green Group 143A.

*Receptacle.*—Color commonly near Yellow-Green Group 144B. — length: approximately 0.5 cm on average. — width: approximately 1.0 cm on average. — surface: smooth. — shape: abroad funnel shaped.

*Peduncle.*—Length: approximately 5.0 cm on average. — width: typically between 0.2 cm to 0.3 cm. — surface: smooth. — color commonly near Yellow-Green Group 144A more or less suffused with near Greyed-Red Group 178A.

*Flower.*—Diameter when open: approximately 7.5 cm. — shape: flat cup shaped. — shape when viewed from above: rounded. — shape of the upper part of the flower profile: flat. — shape of the lower part of the flower profile: concave. — type: very double. — number of petals under normal conditions: commonly between 120 to 140 petals (including the smaller ones in the center of the flower but which are not petaloids). — petals: shape at the base: external petals are obtuse and internal petals are acute. shape at the top: external petals are rounded and internal petals are obtuse. general shape: external petals are rounded and internal petals are obovate narrow. texture: dry. length: external petals are approximately 3.5 cm on average; internal petals are approximately 3.3 cm on average. width: external petals are approximately 2.6 cm on average; internal petals are approximately 1.5 cm on average. — undulation of the petal: very weak. — reflexing of the petal: absent. — petal incision: absent. — petal arrangement: imbricated with half curved petaloids (crescent moon shape). — petal drop: petals drop off cleanly before drying. — fragrance: none. — discoloration of the flower none. — color when opening: basal spot on the upper surface: commonly near Yellow Group 3C. upper surface: external petals are commonly near Red-Purple Group 65C covered with near Red-Purple Group 67C on around 2 mm along the edge of the petal; internal petals are commonly near Red Group 49C very lightly suffused with near Red Group 49B along the edges of the petal. basal spot on the under surface: commonly near Yellow Group 3C. under surface: external petals are commonly near Red-Purple Group 65C strongly covered with near Red-Purple Group 67C; internal petals are commonly near Red Group 49C very strongly covered with near a color between Red-Purple Group 65A and Red Group 49A. — color of the open flower: basal spot on the upper surface: commonly near Yellow Group 3C. upper surface of the flower external petals are commonly near Red-Purple Group 65C covered with near Red-Purple Group 68A on around 2 mm along the edge of the petal; internal petals are commonly near Red Group 49C with a very slight shade of near Red-Purple Group 65D along the edges of the petal. basal spot on the under surface: commonly near Yellow Group 3D. under surface of the flower external petals are commonly near Red-Purple Group 65C strongly covered with near a color between Red-Purple Group 68A and Red-Purple Group 67C; internal petals are commonly near Red Group 49D slightly covered with a shade of near Red-Purple Group 65D. — anthers: number is typically 30 to 40, length is approximately 0.2 cm on average, width is approximately 0.1 cm on average, coloration is commonly near Yellow-Orange Group 14B, and arrangement is regular around styles. — filaments: length is typically between 0.1 cm and 0.5 cm and coloration is commonly near Yellow Group 5C. — styles: length is typically between 0.3 cm to 1.0 cm, coloration is commonly Yellow-Green Group 147D with a touch of Red Group 37A at the junction point with the stigma, and number is typically between 70 to 80. — stigmas: length is commonly less than 0.1 cm and coloration is commonly near Yellow Group 7C. — pollen: color is commonly near Yellow-Orange Group 21B; amount is abundant. — hips: width is approximately 1.7 cm on average, length is 1.4 cm on average, color is commonly near a color between Orange-Red Group 32A and Greyed-Orange Group 169A, and shape is pitcher shape.

Development:

*Vegetation.*—Very strong.

*Blooming.*—Very early in the season, normal to recurrent typically from May to October in France.

*USDA hardiness zone.*—Zone 5.

*Tolerance to disease.*—Good, and particularly against rust (*Phragmidium* sp).

The new 'MEIBRITTY' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEIBRITTY' characterized by the following combination of characteristics:

(a) forms flowers with a cream-ochre colored center and pink colored towards the external petals, (b) produces very double flowers, and (c) exhibits a climbing growth habit;

substantially as herein shown and described.

* * * * *

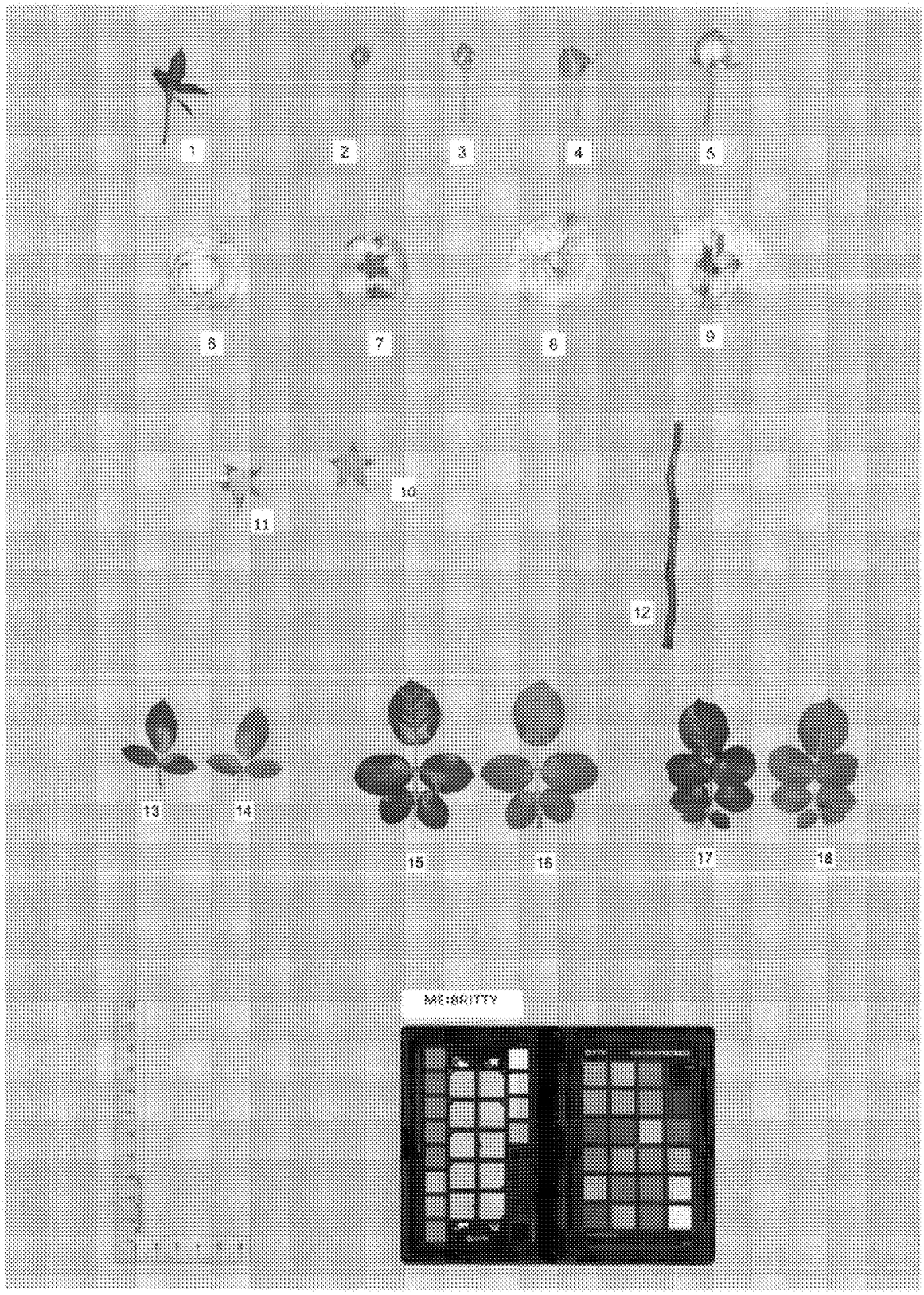
1
2
3
4
5
6
7
8
9
10
11
12
13
14
15
16
17
18
MEIGRITTY